United States Patent
Luciano

(10) Patent No.: US 12,239,426 B2
(45) Date of Patent: Mar. 4, 2025

(54) SYSTEMS AND METHODS FOR CONTROLLING A VOLUME OF FLUID WITHIN A PORTION OF A PATIENT'S BODY

(71) Applicant: THE JOHNS HOPKINS UNIVERSITY, Baltimore, MD (US)

(72) Inventor: Mark Luciano, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 275 days.

(21) Appl. No.: 15/999,842

(22) PCT Filed: Feb. 17, 2017

(86) PCT No.: PCT/US2017/018330
§ 371 (c)(1),
(2) Date: Aug. 20, 2018

(87) PCT Pub. No.: WO2017/143161
PCT Pub. Date: Aug. 24, 2017

(65) Prior Publication Data
US 2021/0213260 A1 Jul. 15, 2021

Related U.S. Application Data

(60) Provisional application No. 62/296,708, filed on Feb. 18, 2016.

(51) Int. Cl.
*A61B 5/0225* (2006.01)
*A61B 5/03* (2006.01)
(Continued)

(52) U.S. Cl.
CPC ............ *A61B 5/0225* (2013.01); *A61B 5/031* (2013.01); *A61M 1/77* (2021.05); *A61M 27/00* (2013.01);
(Continued)

(58) Field of Classification Search
CPC .... A61M 27/00; A61M 27/006; A61M 39/10; A61M 2202/0464; A61M 2205/3379;
(Continued)

(56) References Cited

U.S. PATENT DOCUMENTS 5,000,731 A * 3/1991 Wong .................. A61M 27/006
604/9
8,956,379 B2 2/2015 Luciano et al.
(Continued)

FOREIGN PATENT DOCUMENTS

WO WO-0154766 A1 * 8/2001 .......... A61M 27/006

*Primary Examiner* — Ariana Zimbouski

(57) ABSTRACT

The present disclosure relates generally to controlling a volume of fluid within a portion of a patient's body. For example, the present disclosure can relate to the addition or removal of cerebral spinal fluid (CSF) from a portion of the patient's brain. The amount of fluid can be controlled by a system that includes a dual chamber probe and a volume control. One channel can include a drain element to drain the fluid from the portion of a patient's body. The other channel can include a volume changing element to facilitate the drainage of the fluid by changing a volume of the portion of the patient's body. The volume changing element can be coupled to a volume control, which can control the change of the volume of the portion of the patient's body (e.g., based on passive oscillation or active oscillation).

15 Claims, 4 Drawing Sheets

(51) Int. Cl.
*A61M 1/00* (2006.01)
*A61M 27/00* (2006.01)
*A61M 39/10* (2006.01)

(52) U.S. Cl.
CPC .......... *A61M 27/006* (2013.01); *A61M 39/10* (2013.01); *A61M 2202/0464* (2013.01); *A61M 2205/3379* (2013.01); *A61M 2210/0693* (2013.01); *A61M 2230/04* (2013.01); *A61M 2230/40* (2013.01)

(58) Field of Classification Search
CPC .......... A61M 2230/04; A61M 2230/40; A61M 25/10184; A61B 5/031; A61B 5/023; A61B 5/6852; A61B 5/0225
See application file for complete search history.

(56) References Cited

U.S. PATENT DOCUMENTS

| | | |
|---|---|---|
| 9,011,378 B2 | 4/2015 | Luciano et al. |
| 2003/0212304 A1* | 11/2003 | Lattouf ............... A61M 1/3659 600/17 |
| 2006/0111659 A1 | 5/2006 | Tyler |
| 2009/0177279 A1 | 7/2009 | Luciano et al. |
| 2011/0004158 A1 | 1/2011 | Luciano et al. |

* cited by examiner

SYSTEMS AND METHODS FOR CONTROLLING A VOLUME OF FLUID WITHIN A PORTION OF A PATIENT'S BODY

CROSS-REFERENCE TO RELATED APPLICATIONS

This application is a 35 U.S.C. § 371 U.S. national entry of International Application PCT/US2017/018330, having an international filing date of Feb. 17, 2017, which claims the benefit of U.S. Provisional Application No. 62/296,708, filed Feb. 18, 2016, the content of each of the aforementioned applications is herein incorporated by reference in their entirety.

FIELD OF THE INVENTION

The present disclosure relates generally to controlling a volume of fluid within a portion of a patient's body and, more specifically, to systems and methods for controlling a volume of fluid within a portion of a patient's body using a dual channel probe.

BACKGROUND OF THE INVENTION

Hydrocephalus is a condition characterized by an excessive accumulation of cerebral spinal fluid (CSF) on a patient's brain. The presence of excess CSF on the brain can constrict cerebral blood flow, which can affect intracranial pressure (ICP) and cranial compliance. Many brain disorders, such as dementia and stroke, exhibit some degree of hydrocephalus. In some instances, the excess CSF can be removed from the patient's brain by shunting the fluid through a ventricular catheter. However, shunting alone is not a permanent solution to hydrocephalus.

Accordingly, there is a need in the art for a device to increase and decrease fluid volume within a portion of a patient's body.

SUMMARY OF THE INVENTION

The present disclosure relates generally to controlling a volume of fluid within a portion of a patient's body and, more specifically, to systems and methods for controlling a volume of fluid within a portion of a patient's body using a dual channel probe. The volume can be controlled to facilitate more efficient and physiological fluid removal, to enhance or decrease brain pressure waveforms to effect fluid removal, brain equilibrium, compliance, and/or blood flow, and/or to allow substance delivery under conditions of variable intracranial pressure. The volume of the fluid can be changed in the portion of the patient's body through removal or addition of fluid through the dual channel probe as an open system or a closed system. For example, the open system can remove fluid with simultaneous volume equilibrium for brain homeostasis. The fluid removal can be facilitated with a volume changer. As another example, the fluid removal in the closed system can be based on a biorhythm, such that fluid is added and removed simultaneously to an increase or decrease of a biological parameter (e.g., shown in cyclic pressure waveforms occurring with a cardiac or respiratory body rhythm).

In one example, the present disclosure includes a system that can control a volume of fluid in a portion of a patient's body. For example, the fluid can be CSF located in the patient's brain or spinal cord. The system can include a dual channel probe and a volume control. The dual channel probe can include a drain element to drain the fluid from the portion of a patient's body in one channel of the dual channel probe. The dual channel probe can also include a volume changing element in the other channel of the dual channel probe to control the amount of the fluid in the portion of the patient's body by changing a volume of the portion of the patient's body. The volume changing element can be coupled to a volume control, which can control the change of the volume of the portion of the patient's body (e.g., based on passive oscillation or active oscillation).

In another example, the present disclosure includes a method for control of a volume of fluid in a portion of a patient's body (e.g., CSF within the patient's brain or spinal cord). The method can include inserting a dual channel probe into the portion of the patient's body. The dual channel probe can include a drain element and a volume changing element coupled to a volume control. The volume changing element can be used to change a volume of the portion of the patient's body. The drain element can be used to control an amount of fluid from the portion of the patient's body in response to the change in the volume.

BRIEF DESCRIPTION OF THE DRAWINGS

The accompanying drawings provide visual representations, which will be used to more fully describe the representative embodiments disclosed herein and can be used by those skilled in the art to better understand them and their inherent advantages. In these drawings, like reference numerals identify corresponding elements and.

DETAILED DESCRIPTION

Figure 1:
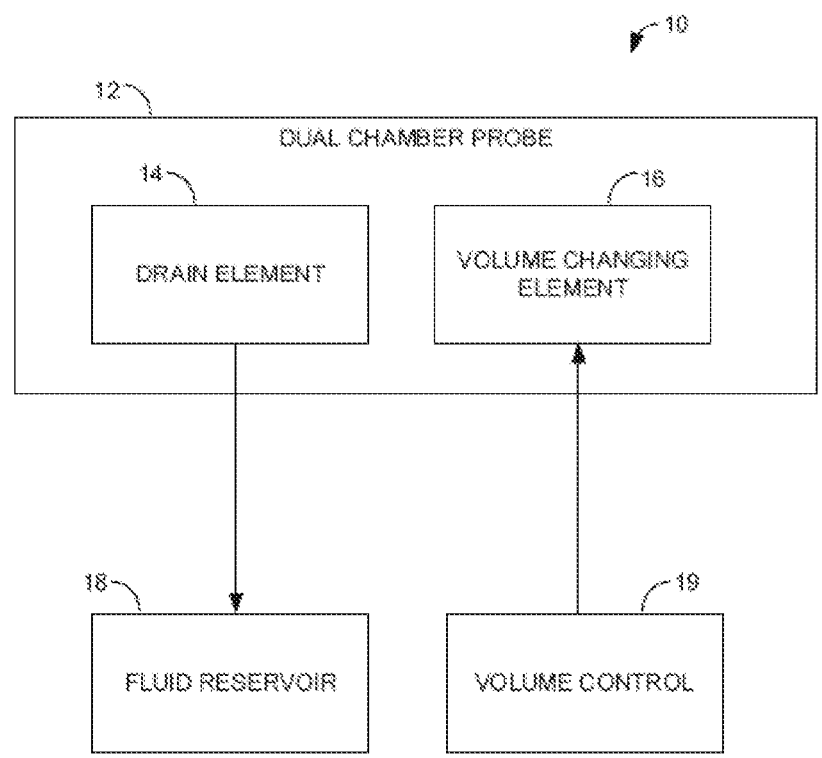
FIG. 1 illustrates a diagram of an example of a system that can control an amount of fluid in a portion of a patient's body in accordance with an aspect of the present disclosure.

The presently disclosed subject matter now will be described more fully hereinafter with reference to the accompanying Drawings, in which some, but not all embodiments of the inventions are shown. Like numbers refer to like elements throughout. The presently disclosed subject matter may be embodied in many different forms and should not be construed as limited to the embodiments set forth herein; rather, these embodiments are provided so that this disclosure will satisfy applicable legal requirements. Indeed, many modifications and other embodiments of the presently disclosed subject matter set forth herein will come to mind to one skilled in the art to which the presently disclosed subject matter pertains, having the benefit of the teachings presented in the foregoing descriptions and the associated Drawings. Therefore, it is to be understood that the presently disclosed subject matter is not to be limited to the specific embodiments disclosed and that modifications and other embodiments are intended to be included within the scope of the appended claims.

The present disclosure relates generally to controlling a volume of fluid within a portion of a patient's body and, more specifically, to systems and methods for controlling a volume of fluid within a portion of a patient's body using a dual channel probe. The dual channel probe can include a drain element and a volume changing element. For example, the drain element can be a ventricular shunt to drain the fluid from the portion of the patient's body, while the volume changing element can expand and contract to change a volume of the portion of the patient's body. The expansion and contraction of the volume changing element can be controlled by a passive volume control system or an active volume control system.

The fluid removal device is unique because it combines the drain element and the volume changing element. The combination of the drain element and the volume changing element can provide at least two methods of changing the pressure within the portion of the patient's body, as well as changing the compliance of the patient's body. The fluid removal device can maximize movement of the fluid from the portion of the patient's body and, in turn, maximize blood flow in the portion of the patient's body. Accordingly, the fluid removal device can be used in the treatment of various diseases where fluid removal is required, such as dementia and other acute and chronic low blood flow states. The fluid removal device can also be used for drug delivery, for example, for tumors, epilepsy, and other neurological diseases.

One aspect of the present disclosure can include a system 10 that can control an amount of a fluid within a portion of a patient's body. As an example, the system can remove cerebrospinal fluid (CSF) from CSF space within the patient's brain or spinal cord. By adding or removing CSF, the system 10 can treat ailments including altered intracranial compliance, decreased cerebral blood flow, and/or abnormal intracranial pressure. Such conditions can occur with head injuries, aging, cerebrovascular disease, brain atrophy, post brain hemorrhage and infection, vasospasms, congestive heart failure, carotid endarterectomy, carotid occlusion/stenosis, cardiopulmonary bypass procedure, hydrocephalus, stroke, dementia, or migraine headaches. Hydrocephalus can be chronic hydrocephalus, normal pressure hydrocephalus, pseudotumor, cerebri, or slit ventricle syndrome.

The system 10 can include a dual chamber probe 12, which can include a drain element 14 in the first chamber and a volume changing element 16 in the second chamber. It will be understood that the dual chamber probe 12 may have additional chambers and is not limited to just two chambers. In some instances, when the system 10 is configured to control an amount of cerebrospinal fluid (CSF) from CSF space (e.g., a ventricle) within the patient's brain or spinal cord, the dual chamber probe 12 can be in the form of a catheter. For example, the catheter can be a ventricular catheter that includes a length of biocompatible tubing with a plurality of holes formed therethrough. The catheter (dual chamber probe 12) can be a multi-lumen catheter with the drain element 14 being a first lumen and the volume changing element 16 being a second lumen. For example, the second lumen can include a deformable element (e.g., a bag, a bladder, a balloon, or the like) that expands and contracts by inflation and deflation to change the volume of the CSF space to facilitate drainage of an amount of CSF by the first lumen. In other words, the two lumen of the catheter can operate together to drain an amount of CSF from the patient's brain, for example, to maximize cerebral blood flow or other cerebral or spinal property. In some examples, second lumen can be located at a tip of the distal end of the catheter.

In the general sense, the dual chamber probe 12 can include a drain element 14, which can drain the fluid from the portion of the patient's body or add the fluid to the portion of the patient's body. In some instances, the drain element 14 can be a passive drain. For example, the drain element 14 can have an open distal end that can be inserted into the portion of the patient's body to receive and drain the fluid. The other end of the drain element 14 can be in fluid communication with a flexible tube, which can carry the fluid out of or into the patient's body. The flexible tube can be connected to a fluid reservoir 18, which can be either external to the patient's body or internal to the patient's body (e.g., within the patient's abdomen). The fluid reservoir 18 can hold the drained fluid. In other instances, the drain element 14 can be in two-way communication with the fluid reservoir 18. In other words, the fluid reservoir 18 can include the fluid that can be added to the portion of the patient's body. The drain element 14 can be used to add the fluid to the portion of the patient's body.

The addition and removal of the fluid by the drain element 14 can be used to modulate the volume of the portion of the patient's body (e.g., modulating the volume of CSF space in the patient's brain or spinal cord). The addition and removal can be facilitated by a change in volume of the portion of the patient's body. Accordingly, the dual chamber probe 12 can include a volume changing element 16 can expand and contract to modulate the volume of the portion of the patient's body. For example, the volume changing element 16 can expand and contract to modulate the volume as much as 2 cubic centimeter ("cc"). In other examples, the volume changing element 16 can expand and contract to modulate the volume as much as 1.5 cc. In still other examples, the volume changing element 16 can expand and contract to modulate the volume as much as 1 cc. The changing volume can facilitate the drainage (or addition) of the fluid from the portion of the patient's body through the drain element 14.

In some instances, the volume changing element 16 can include a deformable element (e.g., a bag, a bladder, a balloon, or the like) that expands and contracts by inflation and deflation to change the volume of the portion of the patient's body. The volume changing element 16 can expand and contract to any size depending on the application, the patient, and/or the portion of the patient's body to facilitate removal of the fluid from the portion of the patient's body. As an example, the volume changing element 16 can inflate to a length of about 10 to about 50 mm and a width of about 5 mm to about 20 mm. As another example, the volume changing element 16 can inflate to a length of about 5 mm to about 10 mm and a width of about 1 mm to about 10 mm.

The volume changing element 16 can be communicatively coupled to a volume control 19. For example, the volume changing element 16 and the volume control 19 can be coupled together with a substance. In other words, the volume changing element 16 and at least a portion of the volume control 19 (as well as the connection between the two) can include a substance, like a fluid (e.g., a biocompatible fluid like saline), a gas, or another malleable substance. Movement of the substance (e.g., triggered by the volume control 19) can trigger the volume changing element 16 to inflate or deflate. The volume control 19 can be located internal to the patient's body and/or external to the patient's body. In some examples, a portion of the volume control 19 can be located internal to the patient's body and another portion of the volume control 19 can be located external to the patient's body.

Figure 2:
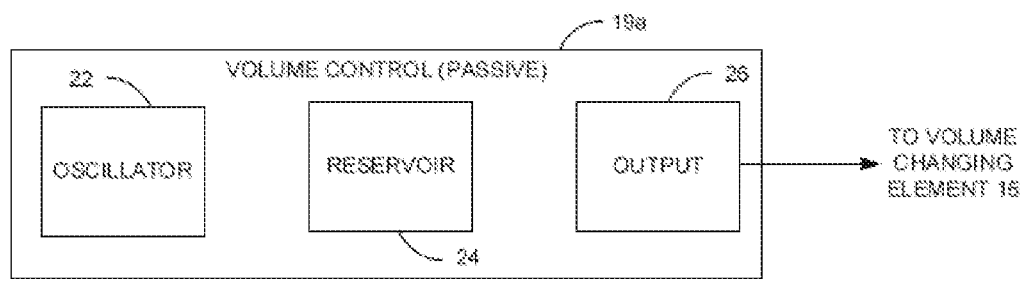
FIG. 2 illustrates a diagram of an example of a passive volume control.

As shown in FIG. 2, the volume control 19*a* can be a passive system. The passive volume control 19*a* can include, for example, an oscillator 22, a reservoir 24, and an output 28 to the volume changing element 16. The oscillator 22 can be operational to control the change of the volume of the portion of the patient's body by oscillating at a set oscillation frequency. In other words, the oscillator 22 can regulate the expansion and contraction of the volume changing element 16 to change the volume of the patient's body. When the oscillator 22 oscillates, the reservoir 24 can output a portion of the substance within to the volume changing element 16 through the output 26. In some instances, the output 26 of the passive volume control 19*a* can also input the substance to the reservoir 24 from the volume changing element 16 during other portions of the oscillation.

Figure 3:
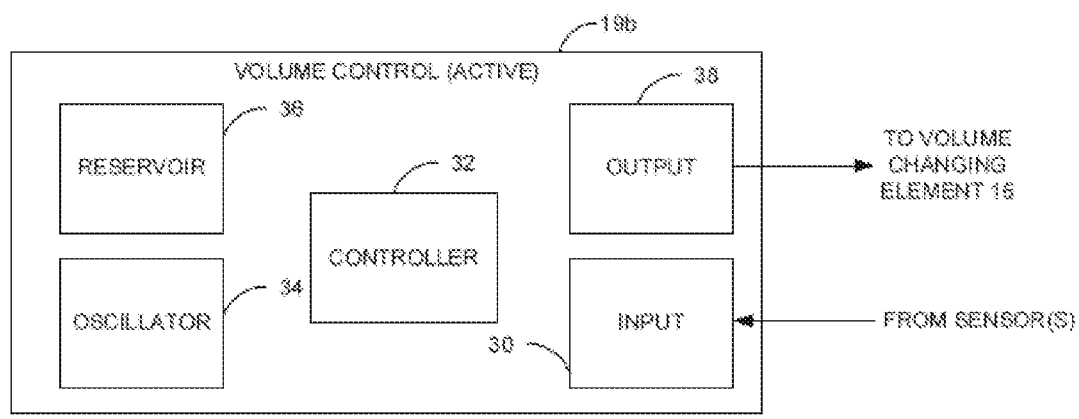
FIG. 3 illustrates a diagram of an example of an active volume control.

As shown in FIG. 3, the volume control 19*b* can be an active system. The active volume control 19*b* can signal the volume changing element 16 to inflate or deflate in response to the input biorhythm. By controlling the change of the volume of the portion of the patient's body, based on the detected biorhythm, the volume control 19*b* can ensure that a proper amount of fluid is located within the volume of the patient's body The active volume control 19*b* can include an input 30, which receives am input signal from at least one sensor. The at least one sensor can detect at least one parameter corresponding to the biorhythm. Examples of biorhythms include a cardiac rhythm of the patient, a cardiac cycle of the patient, a cardiac sequence of the patient, an electrocardiogram of the patient, a pulse oximetry of the patient, a respiratory rate of the patient, or the like. The input 30 can send the signal (either preprocessed or raw) to a controller 32.

The controller 32 can employ an algorithm to trigger the oscillator 34 to oscillate so that the reservoir 36 releases the substance as an output through output 38 to the volume changing element 16. In some instances, the output 38 of the active volume control 19*b* can also input the substance to the reservoir 36 from the volume changing element 16. The oscillator 34, in some instances, can also include a pump (e.g., piston, rotary centrifugal, roller, peristaltic pump, etc.) to pump the fluid, gas, or malleable fluid between the reservoir 36 and the volume changing element 16. The pump can be operational in response to the input or the pumping can operate as a function of the input.

Figure 4:
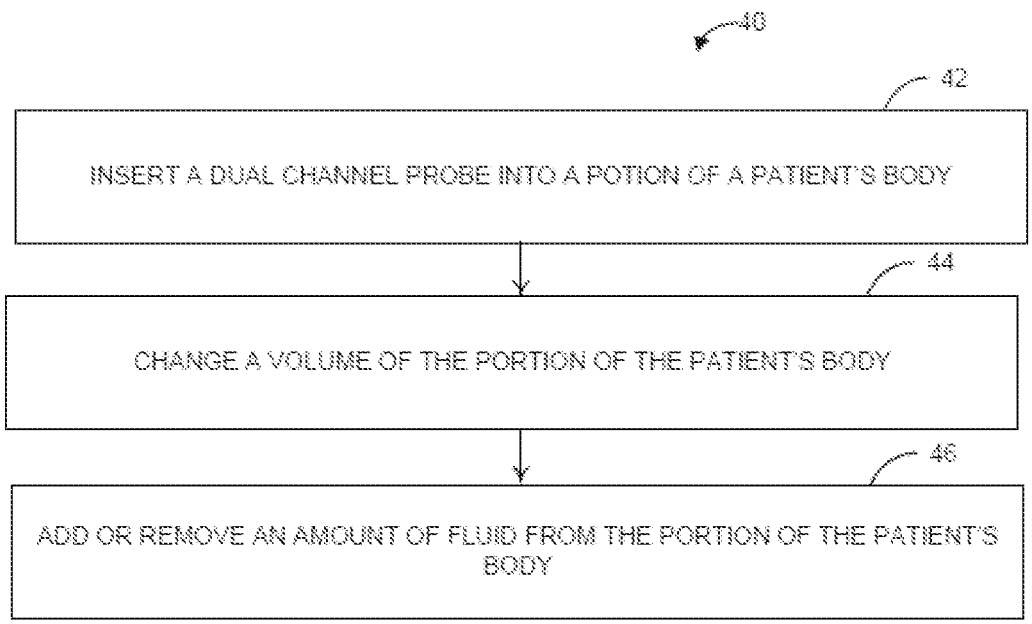
FIG. 4 illustrates a process flow diagram illustrating a method for controlling an amount of fluid within a portion of a patient's body in accordance with another aspect of the present disclosure.
Figure 5:
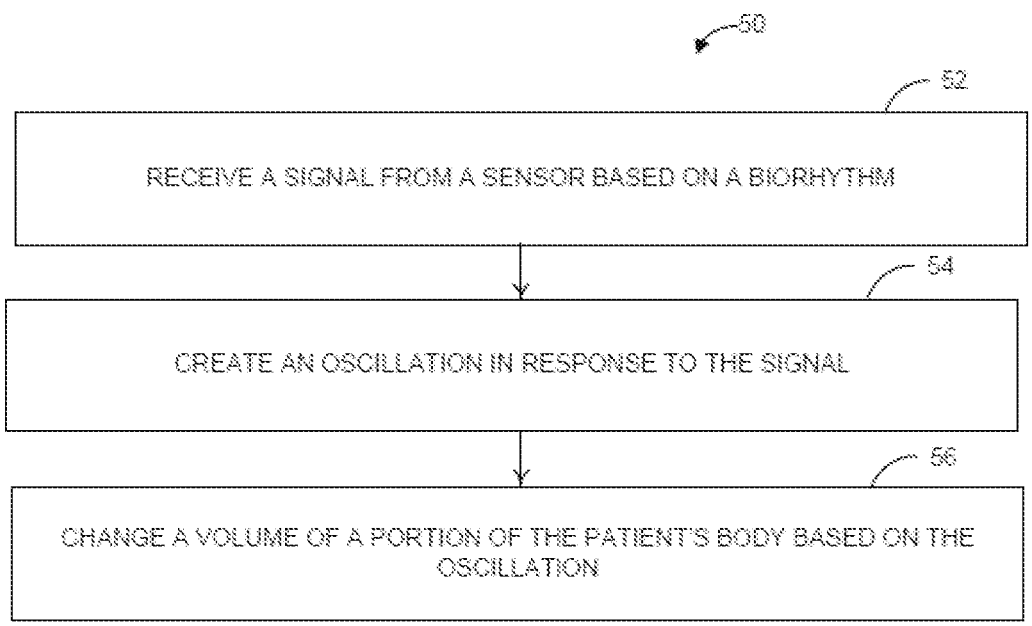
FIG. 5 illustrates a process flow diagram illustrating a method for active volume control.

Another aspect of the present disclosure can include methods 40, 50 for fluid control within a portion of a patient's body, as shown in FIGS. 4-5. As an example, the fluid control of methods 40-50 can be accomplished using the dual chamber probe 12 of system 10, as shown in FIG. 1, which includes a drain element 14 and a volume changing element 16 coupled to a volume control 19 (either active or passive) that operate together to facilitate the fluid removal. The volume can be controlled to facilitate more efficient and physiological fluid removal, to enhance or decrease brain pressure waveforms to effect fluid removal, brain equilibrium, compliance, and/or blood flow, and/or to allow substance delivery under conditions of variable intracranial pressure. The volume of the fluid can be changed in the portion of the patient's body through removal or addition of fluid through the dual channel probe as an open system or a closed system. For example, the open system can remove fluid with simultaneous volume equilibrium for brain homeostasis. The fluid removal can be facilitated with a volume changer. As another example, the fluid removal in the closed system can be based on a biorhythm, such that fluid is added and removed simultaneously to an increase or decrease of a biological parameter (e.g., shown in cyclic pressure waveforms occurring with a cardiac or respiratory body rhythm).

The methods 40-50 are illustrated as process flow diagrams with flowchart illustrations. For purposes of simplicity, the methods 40-50 are shown and described as being executed serially; however, it is to be understood and appreciated that the present disclosure is not limited by the illustrated order as some steps could occur in different orders and/or concurrently with other steps shown and described herein. Moreover, not all illustrated aspects may be required to implement the methods 40-50.

FIG. 4 illustrates a method 40 for fluid removal from a portion of a patient's body. In some instances, the fluid can be excess CSF located within the patient's brain (e.g., in a vesicle of the patient's brain) or spinal cord. At 42, a dual channel probe (e.g., dual chamber probe 12) can be inserted into the portion of the patient's body. At 44, the volume of the portion of the patient's body can be changed. For example, the volume changing element 16 of the dual chamber probe 12 can expand or contract to change the volume of the portion of the patient's body. As an example, the volume changing element 16 can expand or contract in response to receiving a substance (e.g., a fluid, a gas, a malleable substance, or the like) from a volume control 19 (e.g., in response to oscillations, either active or passive). At 46, an amount of fluid can be added to or removed from the portion of the patient's body (e.g., through drain element 14 of dual chamber probe 12). The addition or removal of the amount of fluid can maximize blood flow through the portion of the patient's body or increase compliance of the portion of the patient's body.

The addition or removal can be facilitated by the volume changing element 16 of the dual chamber probe 12. For example, the volume changing element 16 can expand or contract to change the volume of the portion of the patient's body (e.g., modulating the volume by as much as 2 cc) so that the drainage occurs through the drain element 14. In some instances, when the volume control 19 is an active volume control, the expansion and contraction can be coordinated with a biological input (e.g., a cardiac rhythm of the patient, a cardiac cycle of the patient, a cardiac sequence of the patient, an electrocardiogram of the patient, a pulse oximetry of the patient, a respiratory rate of the patient, a biorhythm of the patent, or the like).

A method 50 for active volume control (e.g., by active volume control 19*b* of FIG. 3) is shown in FIG. 5. At 52, a signal (e.g., including a biological input, related to a cardiac rhythm of the patient, a cardiac cycle of the patient, a cardiac sequence of the patient, an electrocardiogram of the patient, a pulse oximetry of the patient, a respiratory rate of the patient, a biorhythm of the patent, or the like) can be received (e.g., by input 30 of active volume control 19*b*). At 54, an oscillation (e.g., by oscillator 34) can be created in response to the signal (e.g., based on an algorithm employed controller 32). The algorithm can, for example, set a threshold over which the oscillator is to oscillate. The threshold can vary based on the number of sensors detecting the biorhythms, the biorhythms being detected, the application, the patient, and the amount of fluid in the part of the patient's body. At 56, a volume of a portion of the patient's body can be changed (e.g., by inflation or deflation of the volume changing element 16) based on the oscillation. For example, the oscillation can trigger a substance to be output (by output 38) from the reservoir 36 to inflate the volume changing element 16. In another example, the oscillation can trigger the substance to be input (by output 38) to the reservoir 36. This control can allow the volume of the portion of the patient's body to be controlled so that a certain amount of fluid can be added or removed (e.g., by drain element 14).

Figure 6A:
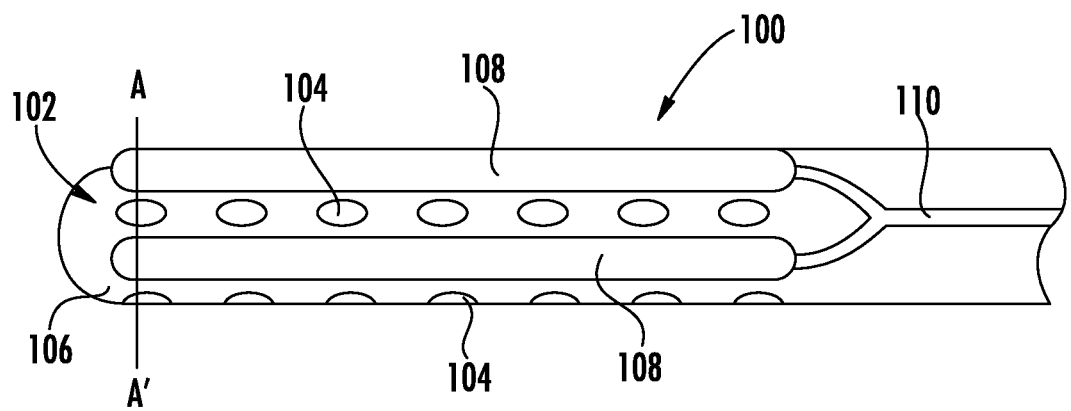
FIG. 6A illustrates a partially sectional view of a catheter according to an embodiment of the present invention.
Figure 6B:
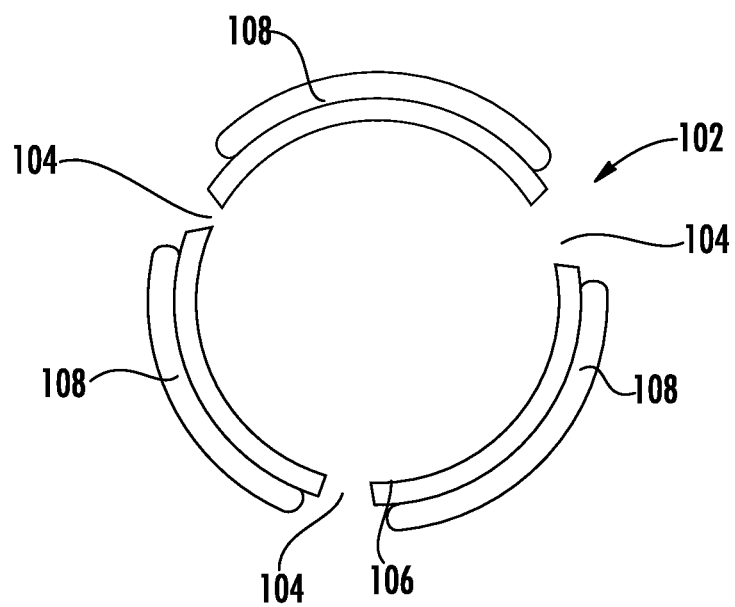
FIG. 6B illustrates a cross sectional view of FIG. 6A taken along axis A-A'.

FIG. 6A illustrates a partially sectional view of a catheter according to an embodiment of the present invention, and FIG. 6B illustrates a cross sectional view of FIG. 6A taken along axis A-A'. As illustrated in FIGS. 6A and 6B the device 100 includes a catheter 102. Catheter 102 includes fluid injection and drainage ports 104. Fluid injection and drainage ports 104 are defined by a wall 106 of the catheter 102. Inflatable balloons 108 are positioned on an external surface of the catheter 102. Air flow into the balloons 106 is provided through a conduit 110 either defined by or adjacent to the wall of the catheter 102. The air flow into the balloons 108 is gaited to cardiac pulse. Further, CSF drainage or fluid injection can be achieved with the catheter 102 and the fluid injection and drainage ports 104. The fluid injection and drainage ports are in fluid communication with a drain and/or a source of sterile fluid for injecting into the space. The balloons 108 are also used to modulate the volume in the space, especially depending on pulse and other fluctuations in volume.

The many features and advantages of the invention are apparent from the detailed specification, and thus it is intended by the appended claims to cover all such features and advantages of the invention which fall within the true spirit and scope of the invention. Further, since numerous modifications and variations will readily occur to those skilled in the art, it is not desired to limit the invention to the exact construction and operation illustrated and described, and accordingly all suitable modifications and equivalents may be resorted to, falling within the scope of the invention.

What is claimed is:

1. A system comprising:
a dual chamber probe, wherein the dual chambers of the probe are configured to be disposed within a portion of a patient's body, comprising:
a first channel comprising a drain element in a first chamber to add or remove fluid from the portion of the patient's body;
a second channel comprising a volume changing element in a second chamber to modulate a volume of the portion of the patient's body to facilitate addition or removal of the fluid, wherein the volume changing element is configured to be positioned within the portion of the patient's body where the volume is to be modulated, such that the volume changing element directly affects the volume of the portion of the patient's body, and wherein a change in the volume of the portion of the patient's body causes fluid to be drained via the drain element in the first channel;
a volume control coupled to the volume changing element to control a modulation of the volume of the portion of the patient's body; and,
a fluid reservoir, wherein the fluid reservoir is in two-way communication with the drain element, such that the fluid from the portion of the patient's body can be stored in the fluid reservoir and the fluid can be added back to the portion of the patient's body on demand in response to the changes to the volume of the portion of the patient's body effected by the second channel's response to the volume control.

2. The system of claim 1, wherein the volume changing element and a portion of the volume control are coupled together with a substance, wherein the substance comprises a fluid, a gas, or a malleable substance.

3. The system of claim 1, wherein the volume control comprises a passive oscillator to control the modulate of the volume of the portion of the patient's body at a set oscillation frequency.

4. The system of claim 1, wherein the volume control comprises an active oscillator to control the modulation of the volume of the portion of the patient's body in response to an input from a sensor, wherein the sensor detects a parameter related to a biorhythm.

5. The system of claim 4, wherein the parameter related to the biorhythm is a parameter related to at least one of a cardiac rhythm of a patient, a cardiac cycle of the patient, a cardiac sequence of the patient, an electrocardiogram of the patient, a respiratory rhythm of the patient, and a pulse oximetry of the patient.

6. The system of claim 1, wherein the drain element is connected to a flexible tube to carry drained fluid to the fluid reservoir.

7. The system of claim 1, wherein: the fluid comprises cerebral spinal fluid (CSF), the portion of the patient's body comprises CSF space within the patient's brain or the patient's spinal cord, and the dual chamber probe is a ventricular catheter.

8. The system of claim 7, wherein the volume changing element is located at a tip of the ventricular catheter and configured to inflate and deflate to modulate the volume of the CSF space.

9. The system of claim 7, wherein the ventricular catheter comprises a length of biocompatible tubing with a plurality of holes formed therethrough so that the drain element drains the CSF from the CSF space.

10. A method comprising:
inserting a dual chamber probe into a portion of a patient's body;
using a chamber of the dual chamber probe to modulate a volume of the portion of the patient's body;
controlling an amount of fluid within the portion of the patient's body based on the volume of the portion of the patient's body with another chamber of the dual chamber probe in response to the modulation in volume, wherein the another chamber of the dual chamber probe is configured to be positioned within the portion of the patient's body where the volume is to be modulated, such that the another chamber of the dual chamber probe directly affects the volume of the portion of the patient's body, and wherein a modulation in the volume of the portion of the patient's body causes the amount of fluid to be drained via a drain element in the another chamber of the dual chamber probe; and,
storing the amount of fluid in a fluid reservoir, wherein the fluid reservoir is in two-way communication with the dual chamber probe, such that the amount of fluid can be stored in the fluid reservoir and the amount of fluid can be added back to the portion of the patient's body on demand.

11. The method of claim 10, wherein the chamber of the dual chamber probe that modulated the volume of the portion of the patient's body comprises a volume changing element and the another chamber of the dual chamber probe comprises a drain element, wherein the volume changing element is coupled to a volume control to control the modulation of the volume of the portion of the patient's body.

12. The method of claim 11, wherein the volume control comprises a passive oscillator that modulates the volume of the portion of the patient's body at a set oscillation frequency.

13. The method of claim 11, wherein the volume control comprises an active oscillator that modulates the volume of the portion of the patient's body in response to a sensed biorhythm.

14. The method of claim 13, wherein the active oscillator changes the volume of the patient's body by:
   receiving a signal from a sensor based on the sensed biorhythm;
   creating an oscillation in response to the signal; and
   modulating the volume of the portion of the patient's body based on the oscillation.

15. The method of claim 14, wherein the active oscillator is in fluid communication with the volume changing element and the oscillation causes the volume changing element to inflate or deflate to modulate the volume.

\* \* \* \* \*